United States Patent [19]

Dudek

[11] Patent Number: 4,642,110
[45] Date of Patent: Feb. 10, 1987

[54] DISPOSABLE DIAPER

[76] Inventor: Evelin Dudek, 3318 Sagebrook, Las Vegas, Nev. 89121

[21] Appl. No.: 751,483

[22] Filed: Jul. 3, 1985

[51] Int. Cl.⁴ .............................................. A61F 13/16
[52] U.S. Cl. ................................................ 604/385.1
[58] Field of Search ............... 604/385 R, 385 A, 378, 604/358

[56] References Cited

U.S. PATENT DOCUMENTS

| | | | |
|---|---|---|---|
| 3,386,442 | 6/1968 | Sabee | 604/378 |
| 3,924,626 | 12/1975 | Lee et al. | 604/378 |
| 4,338,938 | 7/1982 | Seavitt | 604/385 A |
| 4,352,355 | 10/1982 | Mesek et al. | 604/385 A |
| 4,381,782 | 5/1983 | Mazurak et al. | 604/385 A |

Primary Examiner—John D. Yasko
Attorney, Agent, or Firm—Walker & McKenzie

[57] ABSTRACT

A disposable diaper for covering the lower torso of the body mainly the waist and crotch area for receiving and retention of waste therein.

The diaper has a top sheet, an absorbent pad, a bottom sheet and is secured around the body by fastening means and sealed to the body by a restraint means to hold waste within.

2 Claims, 11 Drawing Figures

FIG. 3
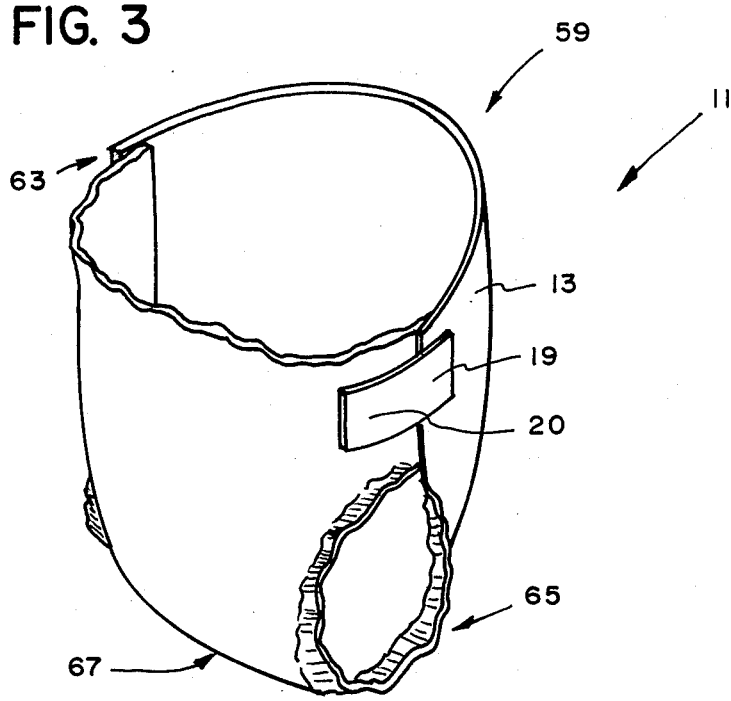
FIG. 4
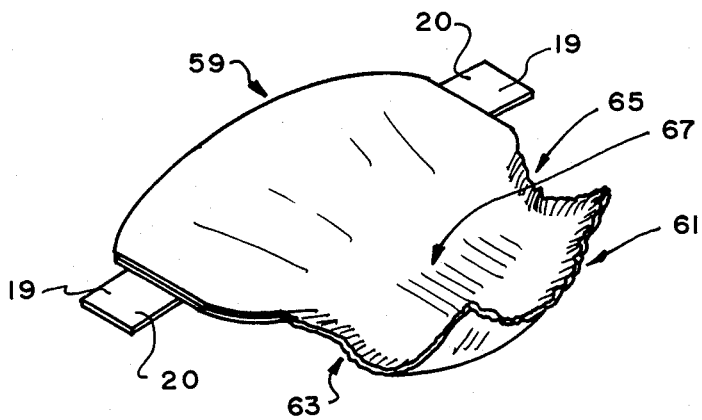
FIG. 6
FIG. 5
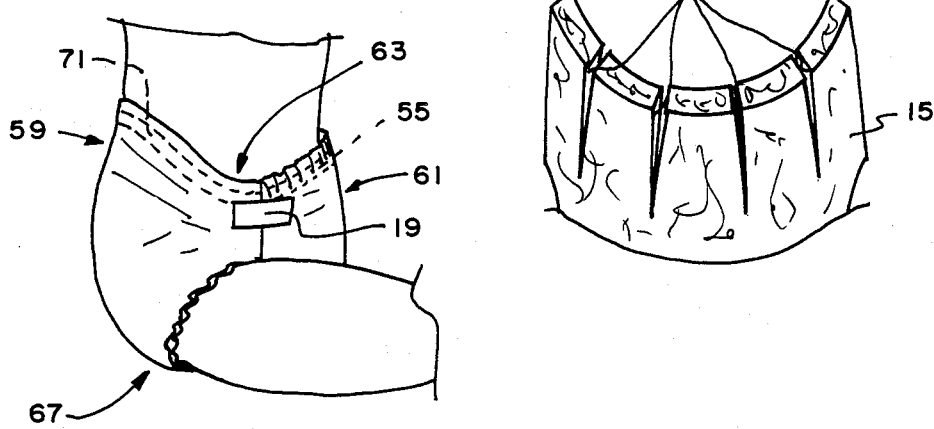

DISPOSABLE DIAPER

BACKGROUND OF THE INVENTION

1. Field of the Invention

The present invention relates to improvements in a disposable diaper for retention of body waste.

2. Description of the Prior Art

Heretofore, various patents have issued for portable garments and devices. See, for example, the following United States Patents: U.S. Pat. No. 4,300,563 granted to Brookfield; U.S. Pat. No. 2,664,895 granted to Shulman; U.S. Pat. No. 2,558,215 granted to Habig et al; U.S. Pat. No. 3,324,856 granted to Young; U.S. Pat. No. 4,182,334 granted to Johnson. Also, various patents have issued for disposable diapers. See, for example, the following United States Patents: U.S. Pat. No. 3,860,003 granted to Buell; U.S. Pat. No. 4,205,679 granted to Repke et al; U.S. Pat. No. 3,995,638 granted to Schaar; U.S. Pat. No. 4,210,143 granted to De Jonckheere; U.S. Pat. No. 4,381,781 granted to Sciaraffa et al; U.S. Pat. No. 4,324,245 granted to Mesek et al. None of the above patents disclose or suggest the present invention.

SUMMARY OF THE INVENTION

The concept of the present invention is to provide a disposable diaper for retention of body waste therein.

A common disadvantage of all known prior disposable diapers is when the diaper is placed around the waist of the body, the enclosed absorbent pad bunches up in the front and back of the diaper. This is not only uncomfortable to the wearer but causes leakage of urine, etc. from around the waist and leg area of the diaper. Also, when the wearer is in a sitting position, the back of the diaper is pulled down showing the lower posterior of the body and leaving a gap between the lower posterior and the diaper.

An object of the present invention is to provide a disposable diaper for retention of body waste therein having the front and back that contours to the body.

Another object of the present invention is to provide sealing pressure to the waist and leg area.

Another object of the present invention is to keep the lower posterior covered while in a sitting position.

Another object of the present invention is to provide a disposable diaper that is comfortable to the wearer and appealing to the eye.

Still another object of the present invention is to provide a lightweight disposable diaper that is relatively easy to manufacture.

The disposable diaper of the present invention includes, in general, a bottom sheet, an absorbent pad for absorbing liquid, a top sheet for comfort to the body, a fastening means, and a restraint means for providing sealing pressure around the waist and legs of the body.

BRIEF DESCRIPTION OF THE DRAWINGS

FIG. 3 is a perspective view of the disposable diaper of FIG. 2 in its configuration as applied to the body.

FIG. 4 is a perspective view of the disposable diaper shown in a relaxed state.

FIG. 5 is a partial perspective view of an end of the absorbent pad showing how it conforms to the body.

FIG. 6 is a right side elevational view of a disposable diaper shown on a person in a sitting position and with only a partial view of the person's body being shown.

DESCRIPTION OF THE PREFERRED EMBODIMENT

Figure 1:
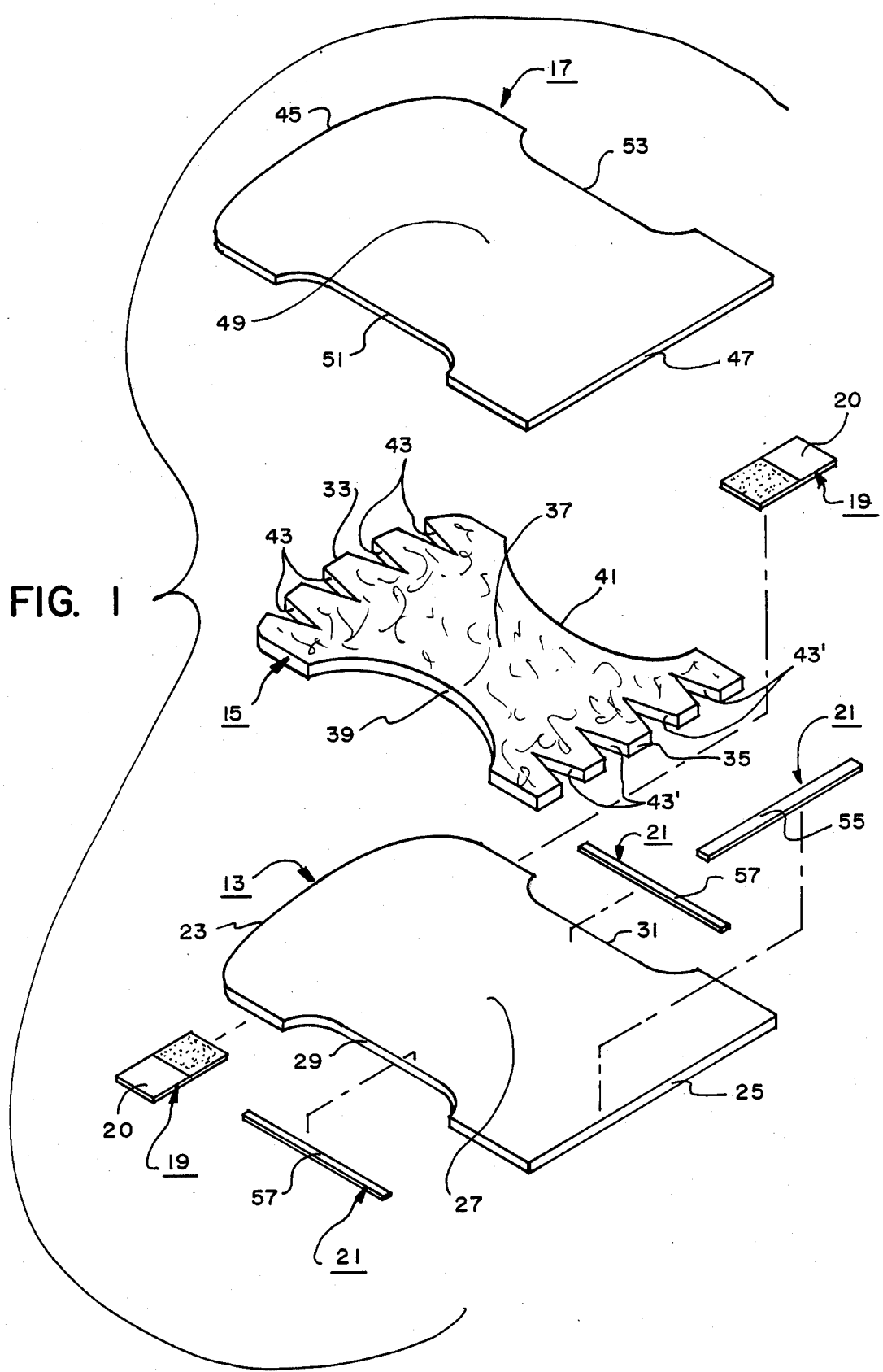
FIG. 1 is an exploded view of the disposable diaper of the present invention.

The disposable diaper 11 of the present invention is for retaining waste excreted from a body. The disposable diaper 11 includes, in general, an elongated bottom sheet 13, an elongated absorbent pad 15, an elongated top sheet 17, a fastening means 19 and a restraining means 21.

Bottom sheet 13 is preferably formed from a thin, flexible water impermeable material such as a low density polyethylene or vinyl film of the type well known to those skilled in the art. The bottom sheet 13 is the exterior of the diaper 11 and includes a first end 23 which is referred to as the back of diaper 11, a second end 25 which is preferred to as the front of diaper 11, an intermediate portion 27 disposed substantially halfway between first end 23 and second end 25, a first side 29 and a second side 31 with first side 29 and second side 31 being in spaced parallel relationship to one another and disposed perpendicular to first end 23 and second end 25. First end 23 of bottom sheet 13 is substantially rounded from the first side 29 extending around to the second side 31 for covering more area of the back when the body is in the sitting position (see, for example, FIG. 1).

Figure 2:
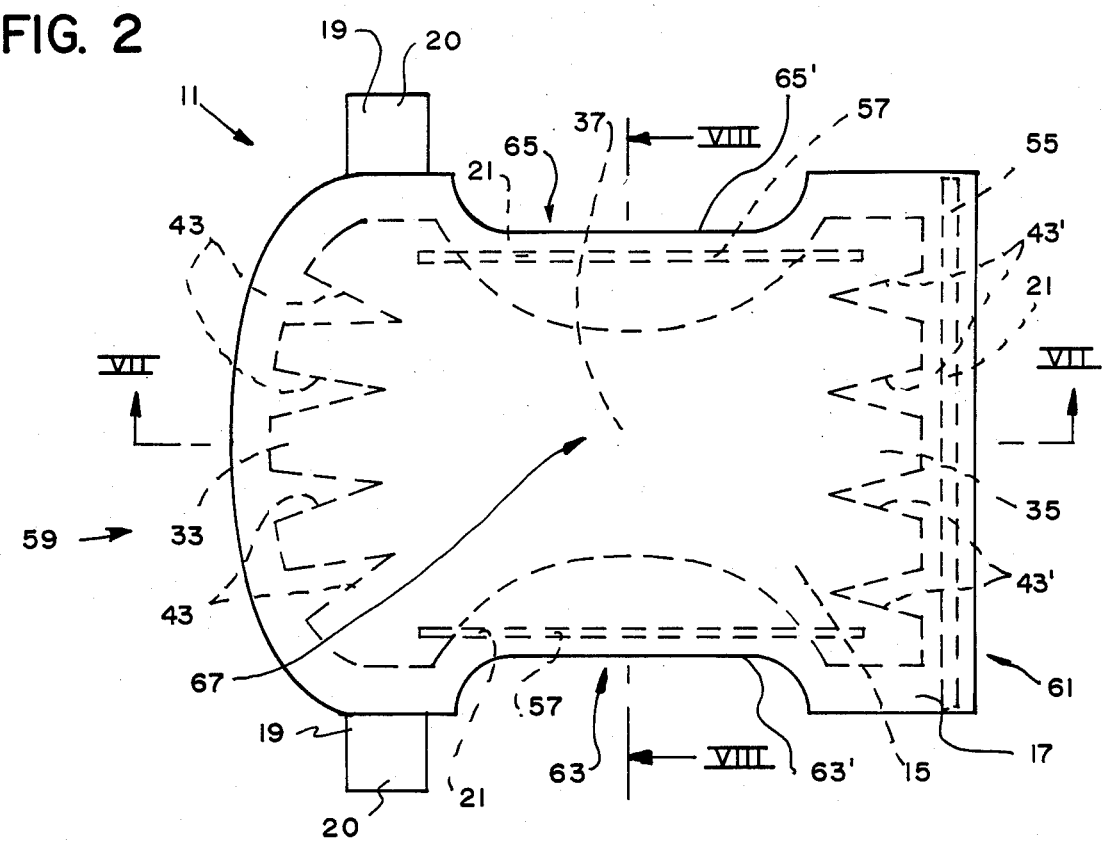
FIG. 2 is a top plan view of the disposable diaper shown in a stretched state.

Absorbent pad 15 is preferably formed from a sheet of absorbent material, such as wood pulp fluff or hydrocellulose material or the like, having a first end 33, a second end 35, an intermediate portion 37, a first side 39 running the entire length between first end 33 and second end 35, and a second side 41 running the entire length between first end 33 and second end 35 disposed in spaced parallel relationship with first side 39. First end 33 is rounded starting from first side 39 and extending around to second side 41 and includes a plurality of notches 43 cut into the rounded first end 33. Notches 43 have a width extending a short distance across the edge of the first end 33 and a depth extending inwardly a short distance toward intermediate portion 37. The width and depth of notches 43 give the notches 43 a V-shape appearance. Notches 43 are evenly spaced in the round first end 33 of absorbent pad 15. The second end 35 of absorbent pad 15 also includes a plurality of V-shaped notches 43' cut into and evenly spaced along the straight edge of the second end 35. The notches 43' are substantially similar in width and depth to the notches 43 of first end 33. Notches 43, 43' allow first end 33 and second end 35 to be gathered around the waist of the body without bunching up of the absorbent pad 15 (see, for example, FIGS. 2, 4 and 5).

Top sheet 17 is preferably comprised of a liquid permeable material such as porous paper or nonwoven fabric sheet of the type well known to those skilled in the art and is disposed next to the skin of the body defining the interior surface of diaper 11. Top sheet 17 includes a first end 45, a second end 47, an intermediate portion 49, a first side 51 extending the entire length between first end 45 and second end 47, and a second side 53 extending the entire length between first end 45 and second end 47 disposed in a spaced parallel relationship with first side 51 thereof. First end 45 of top sheet 17 is substantially rounded in shape and extends from the first side 51 of the first end 45 around to the second side 53 of the first end 45 for providing more covering of the back of the body.

Top sheet 17 is attached to bottom sheet 13 in a manner as to align the edges of first end 45 of top sheet 17 to first end 23 of bottom sheet 13, second end 47 of top sheet 17 to second end 25 of bottom sheet 13, first side 51 of top sheet 17 to first side 29 of bottom sheet 13, second side 53 of top sheet 17 to second side 31 of bottom sheet 13 and attached thereto in any manner well known to those skilled in the art (i.e., such as having glue or the like placed around the perimetrical margin of bottom sheet 13 and adhering top sheet 17 thereto). Absorbent pad 15 is substantially smaller in length and width relative to the length and width of bottom sheet 13 and top sheet 17 and is disposed within a closed cavity between bottom sheet 13 and top sheet 17. Absorbent pad 15 is attached to bottom sheet 13 or top sheet 17 or both by a glue or the like.

Restraint means 21 comprising an elongated elastic member 55 positioned between second end 47 of top sheet 17 and second end 25 of bottom sheet 13 in a prestretched state extends across the second ends 47, 25 and is attached to top sheet 17 and bottom sheet 13 in any manner well known to those skilled in the art, such as being glued or by vulcanization. When the diaper 11 is not held flat, elastic member 55 will cause the bottom sheet 13 and top sheet 17 to gather, as shown in FIG. 3. Elastic member 55 provides sealing pressure around the waist area of the body (see FIG. 6).

Restraint means 21 also includes one or more elastic strips 57 attached by thermo vulcanization or glue disposed between first side 29 of bottom sheet 13 and first side 51 of top sheet 17 and second side 31 of bottom sheet 13 and second side 53 of top sheet 17 for applying sealing pressure around the legs of the body. The elastic strips 57 are attached to diaper 11 in a stretched state (see FIG. 2) and when relaxed will cause bottom sheet 13 and top sheet 17 to gather as shown in FIGS. 3,4 and 6.

The back 59 of diaper 11 comprises rounded first end 23 of bottom sheet 13, rounded first sheet 45 of top sheet 17 and enclosed rounded first end 33 of absorbent pad 15 for concealment of the posterior of the body. Restraint means 21 in addition may include an elastic member 71 which is provided along the back 59 in a similar manner and for the same purpose as elastic member 55 for the front 61 of diaper 11. The front 61 of diaper 11 comprises second end 25 of bottom sheet 13, second end 47 of top sheet 17, enclosed second end 35 of absorbent pad 15, and attached elastic member 55 for concealment of the anterior of the body. The right side 63 of diaper 11 comprises first side 29 of bottom sheet 13, first side 51 of top sheet 17, enclosed first side 39 of absorbent pad 15, and attached elastic strips 57 for concealment of the right side and sealing of the right leg of the body. The left side 65 of diaper 11 comprises second side 31 of bottom sheet 13, second side 53 of top sheet 17, enclosed second side 41 and absorbent pad 15 and attached elastic strip 57 for concealment of the left side and sealing of the left leg of the body. The middle 67 of diaper 11 comprises an intermediate portion 27 of bottom sheet 13, an intermediate portion 49 of top sheet 17, and an intermediate portion 37 of absorbent pad 15 for concealment of the crotch area of the body (see FIGS. 2, 3, 4 and 6).

Right side 63 and left side 65 of middle 67 of diaper 11 is curved inwardly as at 63' and 65' for eliminating excess width of bottom sheet 13, absorbent pad 15 and top sheet 17 in the crotch area.

Fastening means 19 comprises an elongated strip of pressure sensitive adhesive tape 20 of the type well known to those skilled in the art. One strip of adhesive tape 20 is attached to left side 65 at bottom sheet 13 on the side adjacent back 59 in a manner having half of the length of tape 20 extending outwardly therefrom (see FIGS. 2 and 4). Another strip of adhesive tape 20 is attached to right side 63 of bottom sheet 13 on the side adjacent back 59 in a manner having half of the length of tape 20 extending outwardly therefrom. The outwardly extending adhesive tape 20 has a protective covering (not shown) that is removed when diaper 11 is worn. When diaper 11 is worn, the adhesive tape 20 disposed on left side 65 of bottom sheet 13 is attached to left side 65 of bottom sheet 13 at a place adjacent the front 61 (see FIG. 3). Likewise, adhesive tape 20 on the right side 63 is attached to right side 63 of bottom sheet 13 at a place adjacent the front 61 (see FIG. 6).

Waste is contained within diaper 11 by sealing pressure being applied on the skin of the body by elastic member 55 around the waist area and elastic strips 57 around the legs. Also, a neat appearance is provided by notches 43, 43' cut into absorbent pad 15 allowing the enclosed absorbent pad 15 to gather properly (see FIGS. 5 and 6).

Illustrated in FIG. 6 is shown diaper 11 on the body. It should be noticed that the back of the rounded portion of bottom sheet 13, absorbent pad 15 and top sheet 17 extends and covers the back of the body when placed in a sitting position. Also, FIG. 5 shows the gathering of absorbent pad 15 giving diaper 11 a comfortable contour of absorbent pad 15.

Figure 9:
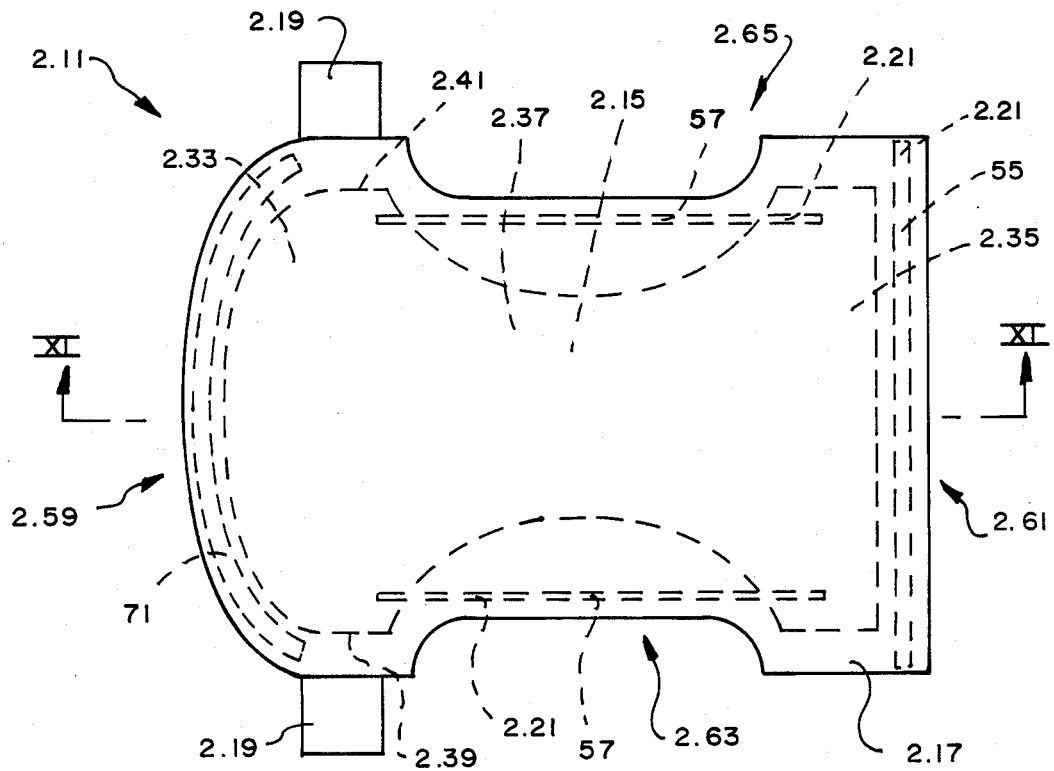
FIG. 9 is a top plan view of another embodiment of the disposable diaper of the present invention.
Figure 7:
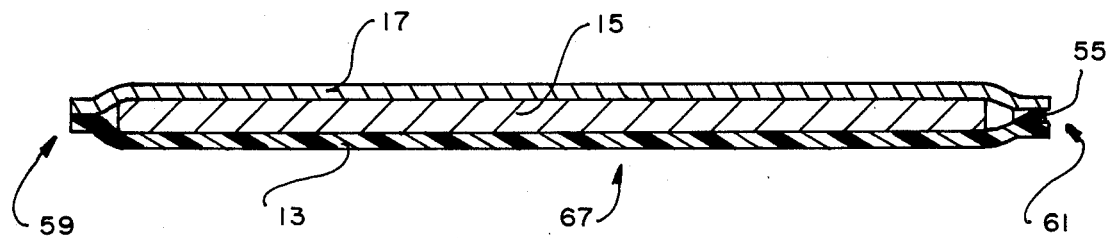
FIG. 7 is an enlarged sectional view substantially as taken on line VII—VII of FIG. 2.
Figure 8:
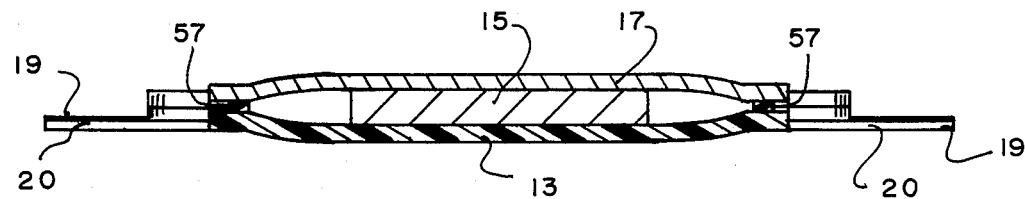
FIG. 8 is an enlarged sectional view substantially as taken on line VIII—VIII of FIG. 2.
Figure 10:
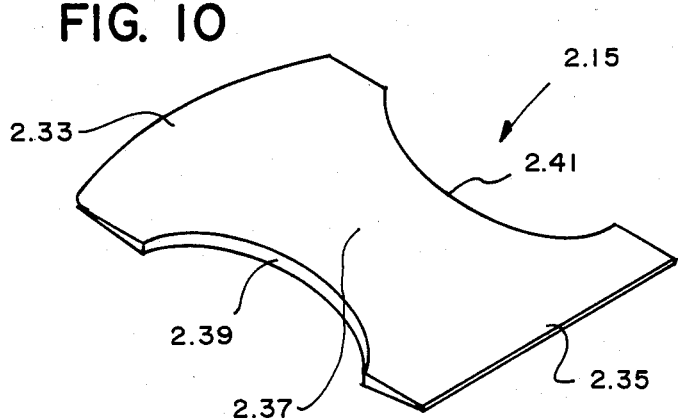
FIG. 10 is a perspective view of an absorbent pad.
Figure 11:
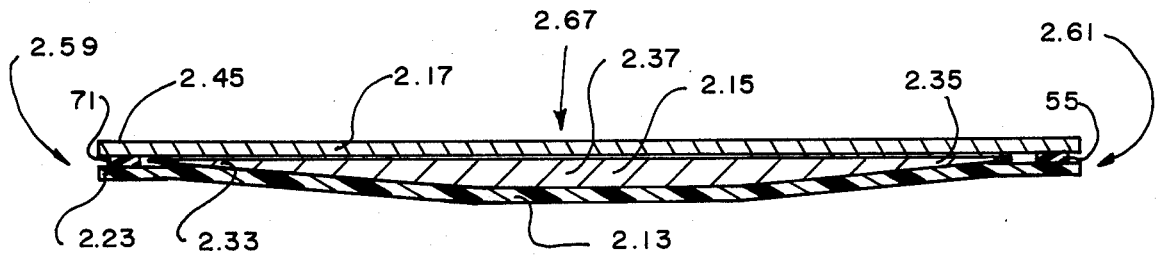
FIG. 11 is a sectional view substantially as taken on line XI—XI of FIG. 9.

FIG. 9 illustrates another embodiment of the present invention and is identified by numeral 2.11. Disposable diaper 2.11 includes, in general, a bottom sheet 2.13, an absorbent pad 2.15, a top sheet 2.17, fastening means 2.19 and restraining means 2.21. The bottom sheet 2.13, top sheet 2.17, fastening means 2.19 and restraining means 2.21 are substantially like the corresponding parts of the previously described diaper 11. Absorbent pad 2.15 as shown in FIGS. 9-11 comprises a first end 2.33 disposed in the back 2.59 of diaper 2.11, a second end 2.35 disposed in the front 2.61 of diaper 2.11, an intermediate portion 2.37 disposed in the middle 2.67 of diaper 2.11, a first side 2.39 disposed in the right side 2.63 of diaper 2.11 and a second side 2.41 disposed in the left side 2.65 of diaper 2.11. Absorbent pad 2.15 has a substantially rounded first end 2.33 starting from first side 2.39 extending around to second side 2.47 thereof and has a gradual decline of the thickness of absorbent pad 2.15 starting substantially from intermediate portion 2.37 and gradually decreasing in thickness extending outwardly to first end 2.33 and second end 2.35 and extending across from first side 2.39 to second side 2.41 (see FIGS. 10 and 11). The decrease in the thickness of the first and second ends 2.33, 2.35 allows the first end and second end to gather around the waist of the body making diaper 2.11 lighter in weight. Elastic member 71 is disposed and attached by glue or thermo vulcanization between first end 2.23 of bottom sheet 2.13 and first end 2.45 of top sheet 2.17 (see FIG. 11). Elastic member 71 extends from the right side 2.63 of diaper 2.11 around to the left side 2.65 of diaper 2.11 for providing additional sealing pressure around the waist of the body.

A smaller absorbent pad (not shown) may be added to the intermediate portion of the diapers 11 and 2.11 having substantially the same width as the intermediate portion and a substantially shorter length in relationship to absorbent pads 15 and 2.15 for increasing the liquid retention of absorbent pads 15 and 2.15 of the diapers 11 and 2.11.

From the foregoing, it will be understood that the disposable diaper provides a good-looking, comfortable diaper that provides a firm leak-proof seal around the waist and legs of the body and covering of the lower back when in a sitting position.

Although the present invention has been described and illustrated with respect to preferred embodiments thereof and a preferred use therefore, it is not to be so limited since changes and modifications can be made therein which are within the full intended scope of the invention.

I claim:

1. A disposable diaper for covering the posterior and anterior of the lower torso of a body for retention of waste therein, said diaper comprising:
    (a) a bottom sheet being liquid impermeable and defining the exterior surface of said diaper;
    (b) an absorbent pad for absorbing liquid; said absorbent pad having a first end, a second end, an intermediate portion, a first side and a second side; said first end of said absorbent pad including V-shaped notches cut into and evenly spaced along said first end of said absorbent pad, said notches having a width extending a short distance across the edge of said first end and having a length extending inwardly toward said intermediate portion of said absorbent pad for allowing said first end of said absorbent pad to conform to the posterior of said body;
    (c) a top sheet being liquid permeable defining the interior of said diaper;
    (d) fastening means for securing said bottom sheet, absorbent pad, and top sheet around the waist of said body; and
    (e) restraint means for applying sealing pressure to the waist and legs of said body.

2. A disposable diaper for covering the posterior and anterior of the lower torso of a body for retention of waste therein, said diaper comprising:
    (a) a bottom sheet being liquid impermeable and defining the exterior surface of said diaper;
    (b) an absorbent pad for absorbing liquid; said absorbent pad having a first end, a second end, an intermediate portion, a first side and a second side; said first end of said absorbent pad being substantially rounded and extending from said first side of said first end around to said second side of said first end thereof; said second end of said absorbent pad being substantially straight across and extending from said first side of said second end across to said second side of said second end;
    said second end of said absorbent pad including V-shaped notches cut into and evenly spaced along said straight second end, said notches having a width extending a short distance across the edge of said second end and a length extending inwardly toward said intermediate portion of said second end of said absorbent pad for allowing said second end to conform to the anterior of said body;
    (c) a top sheet being liquid permeable defining the interior of said diaper;
    (d) fastening means for securing said bottom sheet, absorbent pad, and top sheet around the waist of said body; and
    (e) restraint means for applying sealing pressure to the waist and legs of said body.

* * * * *